US010602963B2

(12) United States Patent
Friedman et al.

(10) Patent No.: US 10,602,963 B2
(45) Date of Patent: Mar. 31, 2020

(54) SYSTEM AND METHOD OF USING LOCATION TECHNOLOGY TO AID PATIENT RECOVERY

(71) Applicant: General Electric Company, Schenectady, NY (US)

(72) Inventors: Bruce A. Friedman, Jasper, GA (US); Matthew Grubis, New Berlin, WI (US); Brian W. Nantz, Menomonee Falls, WI (US); Carl C. Davis, Menomonee Falls, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1196 days.

(21) Appl. No.: 14/792,144

(22) Filed: Jul. 6, 2015

(65) Prior Publication Data
US 2015/0305654 A1    Oct. 29, 2015

Related U.S. Application Data

(62) Division of application No. 12/849,557, filed on Aug. 3, 2010, now Pat. No. 9,104,788.

(51) Int. Cl.
| | |
|---|---|
| *A61B 5/11* | (2006.01) |
| *G06F 19/00* | (2018.01) |
| *G01S 19/01* | (2010.01) |
| *A61B 5/00* | (2006.01) |
| *G01S 17/08* | (2006.01) |
| *G16H 40/20* | (2018.01) |
| *G16H 50/20* | (2018.01) |
| *A61B 5/113* | (2006.01) |
| *G01S 13/46* | (2006.01) |

(Continued)

(52) U.S. Cl.
CPC .......... *A61B 5/1112* (2013.01); *A61B 5/0002* (2013.01); *A61B 5/112* (2013.01); *A61B 5/113* (2013.01); *A61B 5/72* (2013.01); *A61B 5/742* (2013.01); *G01S 17/08* (2013.01); *G01S 19/01* (2013.01); *G06F 19/34* (2013.01); *G16H 40/20* (2018.01); *G16H 50/20* (2018.01); *A61B 2505/09* (2013.01); *G01S 2013/468* (2013.01); *G06F 19/3418* (2013.01); *G07C 1/10* (2013.01); *G07C 9/00111* (2013.01)

(58) Field of Classification Search
CPC .... A61B 5/1112; A61B 5/1113; A61B 5/1114; A61B 5/1115
See application file for complete search history.

(56) References Cited

U.S. PATENT DOCUMENTS

| | | | |
|---|---|---|---|
| 5,652,570 A * | 7/1997 | Lepkofker | ............ A61B 5/1112 340/573.4 |
| 6,135,970 A | 10/2000 | Kadhiresan et al. | |
| 6,838,992 B2 | 1/2005 | Tenarvitz | |

(Continued)

*Primary Examiner* — John R Downey
(74) *Attorney, Agent, or Firm* — Andrus Intellectual Property Law, LLP (57) ABSTRACT

A system for telemetrically monitoring a patient includes a remote monitoring device associated with the patient. A location services system tracks a location of the remote monitoring device. A patient tracking computer calculates a distance and a duration of patient ambulation from the tracked location. A method of monitoring an ambulatory patient monitors the location of a remote monitoring device and derives ambulatory event data from the monitored location.

20 Claims, 6 Drawing Sheets

(51) Int. Cl.
*G07C 1/10* (2006.01)
*G07C 9/00* (2020.01)

(56) References Cited

U.S. PATENT DOCUMENTS

| | | | |
|---|---|---|---|
| 6,847,892 B2 | 1/2005 | Zhou et al. | |
| 6,998,978 B2 | 2/2006 | Kirkeby | |
| 7,091,863 B2 | 8/2006 | Ravet | |
| 7,154,398 B2* | 12/2006 | Chen | G08B 25/016 |
| | | | 340/573.1 |
| 7,328,131 B2 | 2/2008 | Donofrio | |
| 7,978,085 B1 | 7/2011 | Kearns et al. | |
| 2004/0127337 A1* | 7/2004 | Nashner | A61B 5/1036 |
| | | | 482/100 |
| 2005/0258957 A1 | 11/2005 | Krumm et al. | |
| 2005/0270236 A1 | 12/2005 | Krumm et al. | |
| 2007/0085690 A1 | 4/2007 | Tran | |
| 2007/0132577 A1 | 6/2007 | Kolavennu | |
| 2007/0273504 A1 | 11/2007 | Tran | |
| 2008/0001735 A1 | 1/2008 | Tran | |
| 2008/0208446 A1 | 8/2008 | Geelen et al. | |
| 2008/0221928 A1* | 9/2008 | Garcia | G06F 19/3418 |
| | | | 705/3 |
| 2008/0274713 A1 | 11/2008 | Rofougaran | |
| 2008/0281630 A1* | 11/2008 | Sekura | A61B 5/411 |
| | | | 705/2 |
| 2009/0184823 A1 | 6/2009 | Tessier | |
| 2009/0224909 A1 | 9/2009 | Derrick et al. | |
| 2009/0322513 A1 | 12/2009 | Hwang et al. | |
| 2010/0022352 A1 | 1/2010 | Kasama et al. | |
| 2010/0094534 A1 | 4/2010 | Naick et al. | |
| 2010/0097208 A1 | 4/2010 | Rosing et al. | |
| 2010/0097209 A1 | 4/2010 | Wong | |
| 2010/0134276 A1 | 6/2010 | Zaruba et al. | |
| 2010/0141432 A1 | 6/2010 | Sugla | |
| 2010/0249541 A1 | 9/2010 | Geva et al. | |
| 2011/0125514 A1 | 5/2011 | Molaison | |
| 2011/0172904 A1 | 7/2011 | Dayaratne | |
| 2012/0290217 A1* | 11/2012 | Shoval | G06F 19/3418 |
| | | | 702/19 |

\* cited by examiner

SYSTEM AND METHOD OF USING LOCATION TECHNOLOGY TO AID PATIENT RECOVERY

CROSS REFERENCE TO RELATED APPLICATION

This application is divisional of U.S. application Ser. No. 12/849,557, filed Aug. 3, 2010, which application was published on Feb. 9, 2012, as U.S. Publication No. US20120035427, which is incorporated herein by reference in its entirety.

BACKGROUND

The present disclosure is related to the field of telemetry. More particularly, the present disclosure is related to systems and methods of monitoring patient location in order to aid in patient recovery.

Patients recovering in telemetry wards or other hospital settings are often encouraged to exercise, if possible, by walking. Currently, this is merely encouraged or requested of the patient, but no specific demands are made.

In some settings, a patient may be provided with a pedometer that measures distance traveled by the patient over the course of a day, but this information must be manually recorded by a clinician and there is no ability to differentiate types of patient movement.

BRIEF DISCLOSURE

A system for telemetrically monitoring a patient includes a remote monitoring device associated with the patient. The remote monitoring device obtains a physiological value from the patient and broadcasts the physiological value. A location services (LS) system tracks a location of the remote monitoring device. A patient tracking computer is communicatively connected to the remote monitoring device and the LS. The patient tracking computer receives the physiological value and the location of the remote monitoring device and calculates a distance and a duration of a patient ambulation from the received locations.

An alternative embodiment of a system of monitoring an ambulatory patient includes a remote monitoring device associated with the ambulatory patient. A location services (LS) system tracks a position of the remote monitoring device. A patient tracking computer is communicatively connected to the LS system. The patient tracking computer receives the position of the remote monitoring device and the patient tracking computer calculates a distance traveled and an elapsed duration of an ambulatory event from the received positions of the remote monitoring device.

A method of monitoring an ambulatory patient includes providing the ambulatory patient with a remote monitoring device. A location of the remote monitoring device is tracked with a location services (LS) system. An ambulatory event is monitored with a patient tracking computer. The patient tracking computer is communicatively connected to the remote monitoring device and the LS. Ambulatory event data is derived from the tracked location. The ambulatory event data includes an ambulatory event distance and an ambulatory event time.

DETAILED DISCLOSURE

Figure 1:
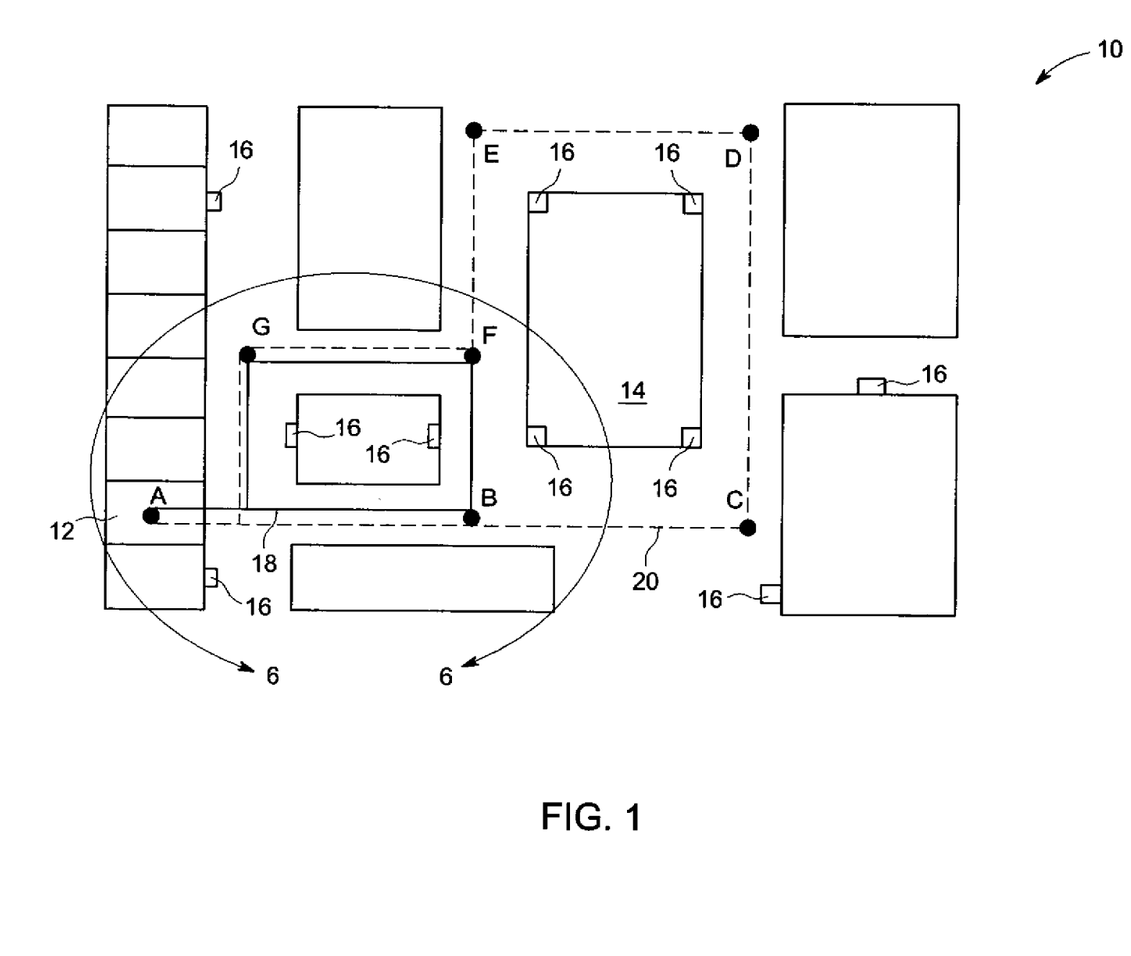
FIG. 1 depicts a floor plan with alternative ambulatory event routes and a plurality of telemetry receivers.

FIG. 1 depicts a floor plan 10 of a telemetry ward or other clinical setting. The floor plan 10 includes a variety of exemplary landmarks on the floor. These landmarks include a patient's room 12 and a nursing station 14. Additionally, the floor plan 10 exemplarily includes a plurality of telemetry receivers 16 disposed throughout the floor plan 10. Embodiments of the systems and methods incorporating one or more of these telemetry receivers 16 will be described in further detail herein. It is to be understood that alternative embodiments do not include a plurality of telemetry receivers 16, as will also be explained in further detail herein.

The floor plan 10 further includes two alternative routes 18, 20 for an ambulatory patient to travel. A short route 18 is represented by a solid line that connects the path A-B-F-G. A long route 20 is represented by a dashed line and follows the path represented by A-B-C-D-E-F-G.

Figure 2:
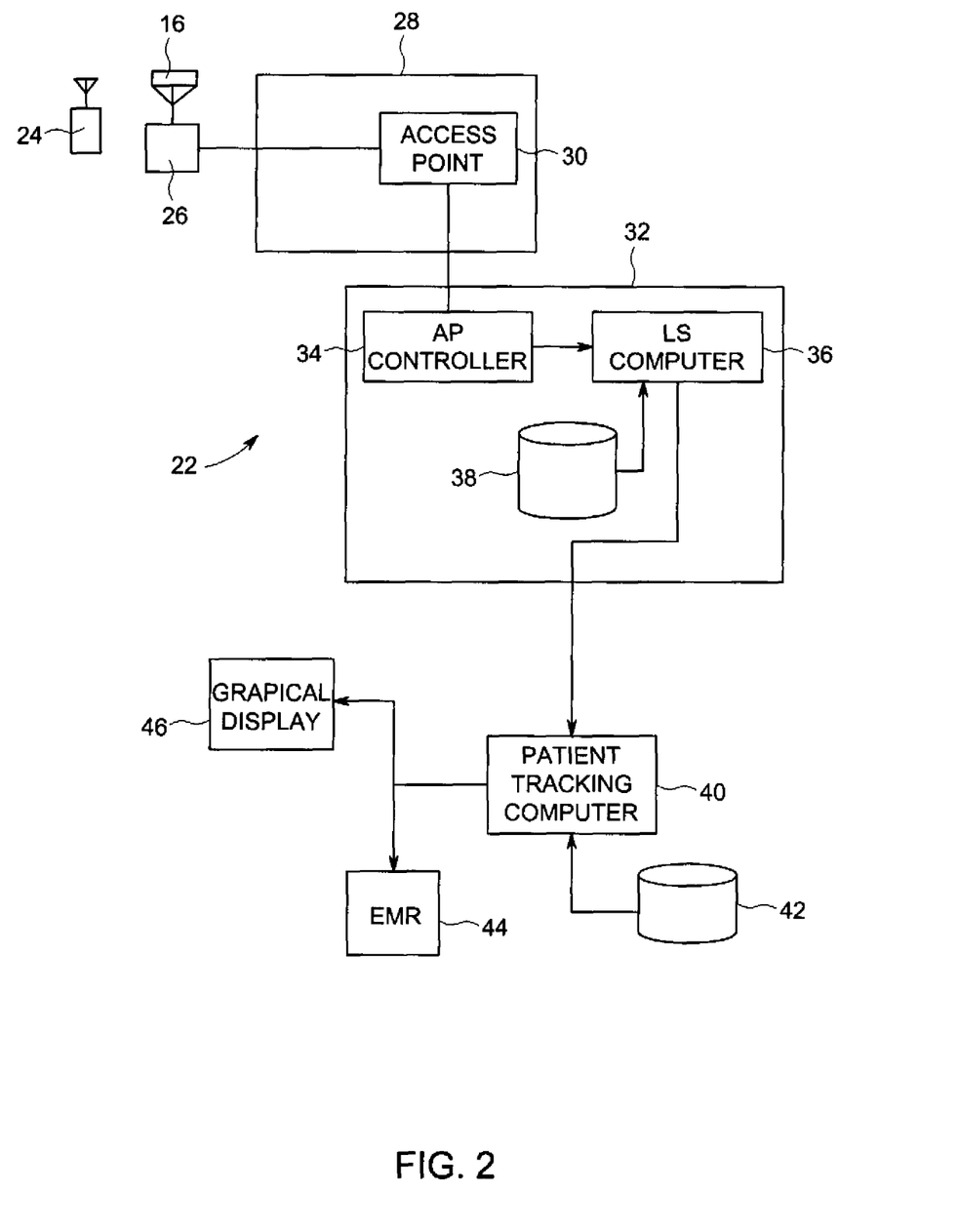
FIG. 2 is a schematic diagram depicting an embodiment of a telemetry system.

FIG. 2 is a schematic diagram of one possible arrangement for a location services (LS) system 22. This includes a remote monitoring device 24. The remote monitoring device 24 is associated with a particular patient within the telemetry ward. In an embodiment, the remote monitoring device 24 is a wireless electronic communication device that is worn or otherwise attached to the patient.

The remote monitoring device 24 broadcasts a location signal in radio frequency (RF) that is indicative of the location of the remote monitoring device 24 and the associated patient. The location signal may take a variety of forms. Non-limiting examples of location signals may include a beacon that is triangulated by beacon sensors, such as telemetry receivers 16. Alternatively, the remote monitoring device 24 may include a global positioning system (GPS) technology such that the remote monitoring device 24 is able to determine a coordinate for its location. The location signal may then be a broadcast of this determined location coordinate. In a still further embodiment, the remote monitoring device may be a physiological monitoring device, as will be described in greater detail herein with respect to an alternative embodiment. In such an embodiment, the remote monitoring device 24 may obtain and broadcast physiological data from the patient. The broadcast signal with the physiological data may also be triangulated in order to determine the location of the remote monitoring device 24.

The technology used by the monitoring device 24 to broadcast the location signal may be any of a variety of known broadcast technology. This includes the above-referenced radio frequency (RF) technology. Alternatively, the location signal may be broadcast in the form of infrared (IR) or ultrasound; however, these are not limiting on the technologies that may be used to broadcast the location signal.

As noted above, embodiments of the location services system 22 may include a plurality of telemetry receivers 16 that receive the signals broadcast by the remote monitoring device 24. It is to be understood that the plurality of telemetry receivers 16 will be designed to receive the type of signal broadcast by the remote monitoring device 24. As such, the telemetry receivers 16 may be receivers configured to receive RF, IR, ultrasound, or other broadcast technology. It is to be further understood that the number and location of telemetry receivers distributed throughout a telemetry ward may be dependent upon the broadcast technology used. Therefore, in some embodiments a plurality of telemetry receivers 16 may be distributed throughout the area, while in other embodiments only a single telemetry receiver may be necessary.

The telemetry receivers 16 are connected to an amplifier that amplifies the signal received by the telemetry receiver 16. Although not depicted, the amplifier 26 may also include other forms of signal conditioning or processing, including, but not limited to, filtering and/or digitization.

Signals from the amplifier 26 are transmitted to a remote closet 28. The remote closet 28 is connected to each of the plurality of telemetry receivers 16 located in a defined area. In one example, the medical care facility includes a telemetry ward that expands to multiple floors of the medical care facility. In such an example, a remote closet 28 may be placed at each of the floors in order to collect and process the signals received by the telemetry receivers 16 on that floor.

The remote closet 28 directs the received location signals from the telemetry receiver 16 to an access point 30. The access point 30 measures the strength of the location signals from the remote monitoring device 24 that are received by one or more telemetry receivers 16. In the location services system 22 wherein a plurality of telemetry receivers 16 are distributed throughout the telemetry coverage area, the strength of the location signals received at each of the telemetry receivers 16 as determined by the access point 30 can be used to triangulate the remote monitoring device as the varying signal strength from a plurality of telemetry receivers 16 may be used to determine the patient location with reference to each of the telemetry receivers 16 receiving the location signal.

The access point 30 of the remote closet 28 provides the location information, including the received signal strengths, to a main closet 32. The main closet 32 collects all of the information from the plurality of remote closets 28 distributed throughout the location services system 22. The access point 30 of the remote closet 28 provides the location information, including the received signal strengths, to the main closet 32 through any number of information transmission technologies, including wired, wireless, or fiber optic technologies. An access point (AP) controller 34 is connected to each of the access points 30 when a plurality of remote closets 28 exist in the location services system 22. The AP controller 34 coordinates the transmission and reception of the location information from the access points 30 of each of the remote closets 28.

The location information is provided from the AP controller 34 to a location services (LS) computer 36. The LS computer includes computer readable code stored on a computer readable medium 38 that embodies software as detailed further herein for calculating location information regarding a patient.

The LS computer 36 operates according to the computer readable code embodied on the computer readable medium 38 such that the LS computer 36 tracks the location of the remote monitoring device 24 based upon a received location signal. The LS computer 36 may track the location of the remote monitoring device 24 as a plurality of locations in real-time (RT), or in near-real-time, as determined by the refresh rates of the access point 30 and AP controller 34, alternatively, the LS computer 36 may track the location of the remote monitoring device 24 at any alternative appropriate time interval as would be recognized by one of ordinary skill in the art. Therefore, some embodiments may refresh the tracked patient location every second, while alternative embodiments may determine location every minute; however, these are merely exemplary and are not intended to be limiting on this disclosure.

The tracked patient location of the remote monitoring device 24 is transmitted from the LS computer 36 of the main closet 32 to a patient tracking computer 40. The patient tracking computer 40 can be connected to a computer readable medium 42 which contains computer readable code that upon execution by the patient tracking computer 40, causes the patient tracking computer 40 to carry out the processes and functions as disclosed herein.

The patient tracking computer 40 receives the plurality of tracked patient locations of the remote monitoring device 24 from the LS computer 36 and calculates at least one of a variety of patient ambulatory event data from the received plurality of tracked patient locations. The ambulatory event data may include a total distance traveled by the remote monitoring device 24.

In order to facilitate data processing, the tracking of the remote monitoring device 24 location may be broken into one or more ambulatory events. Each ambulatory event would have a defined beginning and a defined end. Therefore, the patient tracking computer 40 may determine a distance traveled by the remote monitoring device 24 over the course of an ambulatory event. Alternatively, the patient tracking computer 40 may calculate a time duration of the ambulatory event. In still further embodiments, the patient tracking computer 40 may calculate an average or an instantaneous speed of the patient during the ambulatory event from the calculated distance and the calculated duration, as disclosed above with respect to alternative embodiments.

The patient tracking computer 40 may calculate the ambulatory event data using one or more algorithms stored on the computer readable medium 42. In an exemplary embodiment of the algorithms used to calculate the ambulatory event data, the patient tracking computer may calculate the distance traveled between track patient location as a straight line between the two locations. A more advanced algorithm may be used to calculate the distance traveled as an average distance traveled by tracked patients between similar locations.

In a still further embodiment, which will be described in greater detail herein, and particularly with respect to FIG. 6, the algorithms used by the patient tracking computer 42 to calculate the ambulatory event data may calculate the distance traveled by the patient between two tracked patient locations based upon a probability analysis of various patient paths. Such probabilities may be developed over time by monitoring location information for various ambulatory patients. This patient location information may be analyzed using an advanced neural network (ANN) or Bayesian analysis to determine likely patient routes between two tracked patient locations. These likely patient routes are then used to derive the distance traveled by the patient between the two tracked patient locations. The advanced neural network or Bayesian analysis of historical patient location information may result in an algorithm that consists of probabilities or Gaussian distributions related to the actual path taken by a patient between two tracked patient locations.

The patient tracking computer 40 is communicatively connected to an electronic medical record (EMR) 44 of the patient such that the ambulatory event data may be stored as part of the patient's electronic medical record 44. The recordation of the ambulatory event data in the patient's EMR 44 allows for the ambulatory event data to be used as a physiological parameter to be considered in the evaluation of the patient's medical status. Furthermore, the ambulatory event data calculated by the patient tracking computer 40 may be sent to a graphical display 46. The graphical display 46 presents the calculated ambulatory data to a clinician, the patient, or the patient's friends or family. As will be disclosed in further detail herein, the presentation of ambulatory data to non-medical personnel, such as the patient or the patient's friends and family, may provide additional benefits in expressing the patient's condition and/or progression towards recovery in a non-technical format.

Figure 3:
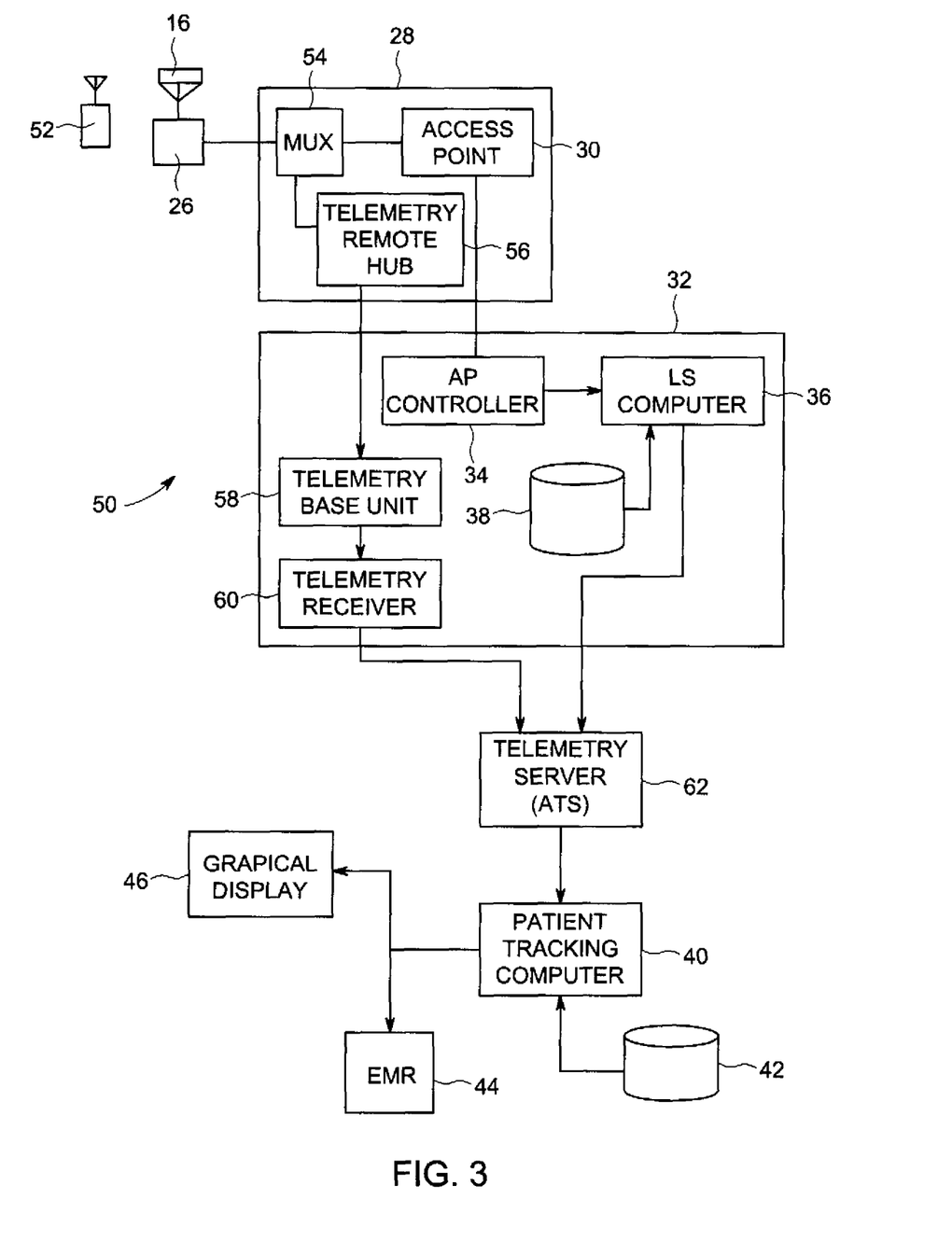
FIG. 3 is a schematic diagram depicting an alternative embodiment of a telemetry system.

FIG. 3 depicts a schematic diagram of a telemetry system 50 that incorporates the location services system 22 (depicted in FIG. 2). It is to be noted that like numerals between FIGS. 2 and 3 represent like elements to which the description with respect to FIG. 2 applies. Therefore, only those new elements found in the telemetry system 50 will be described in greater detail herein with respect to FIG. 3. The telemetry system 50 is an exemplary embodiment of a system wherein an RF signal bearing physiological data from the remotely monitored patient is triangulated and used to identify the patient's location.

The remote monitoring device 52 of the telemetry system 50 further monitors at least one physiological value from the patient and broadcasts the at least one physiological value exemplarily using RF, although other technologies such as IR or ultrasound may be potentially used. A non-limiting example of the types of physiological values that may be obtained by the remote monitoring device 52 includes heart rate, an electrocardiogram (ECG), non-invasive blood pressure (NIBP), and $SpO_2$. However, this list is merely exemplary and is not intended to be limiting on the scope of physiological values that may be obtained from the patient by the remote monitoring device 52.

The remote monitoring device 52 broadcasts the at least one physiological value obtained from the patient. In such an embodiment the location of the remote monitoring device 52 may be derived from the broadcast at least one physiological value. In an alternative embodiment, the remote monitoring device 52 may also broadcast an independent location signal, as described above with respect to FIG. 2. In one such embodiment, the telemetry signals are broadcast at a low frequency and the location signals are broadcast at a high frequency. This facilitates the separation of the broadcasted physiological values from the broadcasted location. In an alternative embodiment the telemetry signals and the location signals are broadcast using two different broadcast modalities. In one exemplary embodiment, the telemetry signal is broadcast in RF while the location signal is broadcast in IR.

The at least one physiological value is transmitted through the telemetry receiver 16 and amplifier 26 to the remote closet 28. A multiplexer 54 receives the broadcast physiological signal and the location information. In one embodiment, the multiplexer 54 separates a lower frequency telemetry signal from a higher frequency location signal and directs the received signals to the appropriate components of the telemetry system 50 for further processing. In an alternative embodiment separate receivers are distributed to receive separate broadcasts of telemetry and location signals.

From the multiplexer 54, the physiological values are provided to a telemetry remote hub 56 that prepares the physiological values for transmission from the remote closet 28 to the main closet 32. The telemetry remote hub 56 may transmit the physiological values to a telemetry base unit 58 in the main closet 32. The telemetry base unit 58 receives and processes the physiological values. In an embodiment, the transmission of the physiological values from the telemetry remote hub 56 to the telemetry base unit 58 is performed by fiber optic transmission technology and the telemetry remote hub 56 and the telemetry base unit 58 perform the signal conditioning required for the optical fiber conversion necessary for the transmission.

After the physiological values are transmitted from the telemetry remote hub 56 to the telemetry base unit 58, the telemetry base unit 58 processes the fiber optic signal to extract the physiological values embedded thereon. The telemetry base unit 58 sends the physiological values to a telemetry receiver 60 that receives physiological values and further directs the physiological values to a telemetry server (ATS) 62. The ATS 62 performs further analysis of the received physiological values, such as to process the received physiological values into appropriate forms for storage and interpretation. Additionally, if the telemetry system 50 is part of a broader system for telemetrically monitoring the physiological condition of a patient, the ATS 62 may derive additional physiological data from the received physiological values and/or apply institutional diagnostic rules such as to perform automatic or automated diagnostic tests or other patient monitoring.

The ATS 62 also receives the broadcast locations of the patient from the LS computer 36. The ATS 62 may coordinate the physiological values and the locations from the patient with other patient, facility, or services information that may be necessary for the operation of other features of the telemetry system 50 that are not central to the present disclosure. Such additional telemetry systems functionalities include patient medical history and EMR access, clinical staff information, medical care facility availability, and facility capacity.

The ATS 62 transmits all of the physiological values and the patient locations to the patient tracking computer 40. In addition to the ambulatory event data calculated by the patient tracking computer 40 as disclosed with respect to FIG. 2, when the patient tracking computer 40 further receives physiological values from the ATS 62, the patient tracking computer may further calculate a correlation or other relationship between the at least one physiological value and the ambulatory event data. Merely exemplary embodiments of such correlations may include a comparison of ambulatory event duration to patient heart rate, $S_pO_2$, or blood pressure. Alternative comparisons may similarly be drawn between the ambulatory event distance and the physiological values noted above.

In still further embodiments, because the distance, duration, and/or speed of the ambulatory event is known, this ambulatory event data may be compared to a physiological value such as a measurement of the patient's ECG. In this embodiment, the ambulatory event monitored by the telemetry system 50 can be analyzed as a form of stress test wherein changes to ECG morphology may be monitored with respect to an ongoing physical stress to the patient. The types of morphological analyses performed on ECG data are known to persons of ordinary skill in the art of stress tests. It is understood that while ECG has exemplarily been identified as the physiological value evaluated in the stress test, alternative physiological values may also be used in this analysis.

The patient tracking computer 40 is connected to the patient's electronic medical record (EMR) 44 such that the results of these correlative analysis may be recorded as part of the patient's electronic file. Similarly, the results of these comparison between ambulatory event data and physiological values may be sent to a graphical display 46 for presentation to clinicians, the patient, or others.

Figure 6:
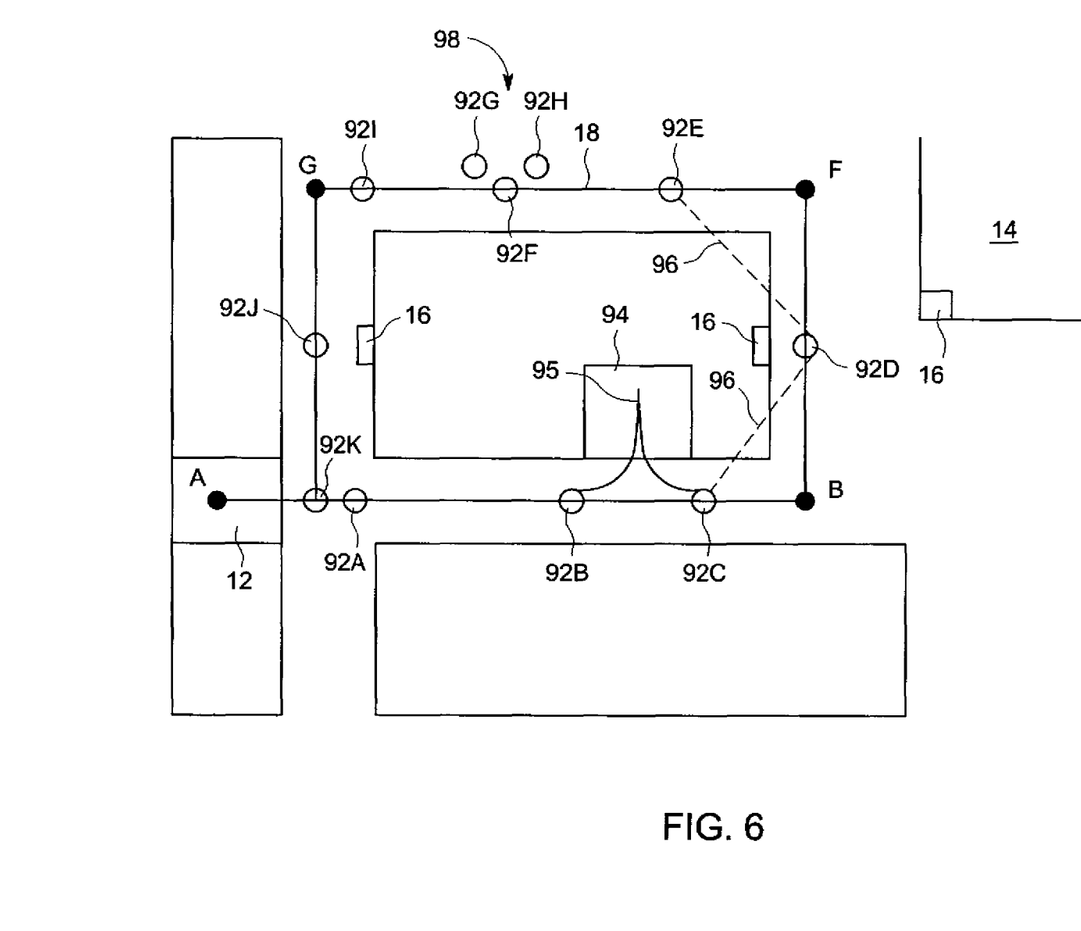
FIG. 6 is a more detailed depiction of a portion of the floor plan of FIG. 1 denoted by line 6-6 of FIG. 1.

FIG. 6 is a more detailed depiction of an embodiment of a portion of floor plan of FIG. 1 denoted by line 6-6 of FIG. 6 will herein be used to describe additional features of embodiments of the system and method for monitoring an ambulatory event. More specifically, the floor plan of FIG. 6 depicts an embodiment wherein the patient location is only intermittently determined or broadcast by the remote monitoring device.

In FIG. 6, a plurality of position beacons 92 A-K denote the actual position of the patient as determined by the location services system. These beacons 92 A-K exemplarily represent constant time intervals. As a merely exemplarily embodiment, the location services system determines actual patient location identified by the beacons 92 A-K once every minute, however, it is understood that the intervals between the beacons 92 A-K may be more or less including intervals that approach or achieve real-time or near-real-time.

Returning to the exemplary embodiment of FIG. 6, the patient completes the short route 18 while on the path of A-B-F-G-A over the course of approximately 11 minutes, as represented by the eleven beacons 92 A-K.

When the patient location is only intermittently derived, algorithms must be implemented in order to sufficiently track the ambulatory event, and accurately monitor the distance traveled by the patient during the ambulatory event.

As mentioned above, the algorithms used to calculate the distance traveled by the patient during the ambulatory event may range in complexity from a simple straight line path between position beacons to a more detailed analysis that incorporates information regarding the likelihood of a patient to travel along a particular path between two position beacons. These algorithms may be derived through an analysis of historical patient movements across a large number of patients on the same ambulatory route or in the same ambulatory ward. Additionally, the algorithms may be nuanced or particularized to specific patients after sufficient ambulatory information for a particular patent is acquired. This historical patient location information may be used to identify percentages or likelihoods that a patient will take a particular path (with a defined distance) between two position beacons. The algorithms used to calculate the distance traveled between two position beacons may be derived using a form of analysis such as an advanced neural network or Bayesian analysis. As noted above, the results of this analysis of historical patient location information may be probability or Gaussian distributions related to particular patient paths between position beacon.

Information regarding the likelihood of patients to choose particular paths and/or destinations may be incorporated into both the tracking of patient location during the ambulatory event and the calculation of the distance traveled during the ambulatory event. For example, a room 94, such as a bathroom, may exist between beacons 92B and 92C. Due to the interval between these two beacons, it may be that the distance traveled by the patient may be accurately represented by a straight line between beacons 92B and 92C. Alternatively, the patient's path may be more correctly represented by line 95 that quickly enters the bathroom 94 and exits the bathroom 94 before the patient's location is determined again.

The above-noted analysis of historical patient location information may identify that it is very unlikely that the patient would enter a room, such as bathroom 94, for only a few seconds, such that a location beacon would not appear in the bathroom 94. Exempilarily, the algorithm may identify that there is a 10% chance that the patient traveled path 95 while there is a 75% chance that the patient traveled directly between 92B and 92C. Thus, in such a situation, it may be accurately reflected that the patient most likely proceeded directly between beacon 92B and 92C during the ambulatory event. A travel distance calculated by the algorithm may be adjusted to account for these percentages, either selecting the distance of the most likely path or by providing a weighted average of the alternative path distances weighted by their likelihood percentages. These models or estimates may be adjusted based upon the patient's average speed or instantaneous speed at the previous beacon (92B). This additional ambulatory event data can promote more accurate tracking of patient ambulation paths and distances.

Another consideration is the specific layout of the short ambulatory route 18 itself. While a direct positional measurement between beacons 92C and 92D would represent the shortest distance between these two adjacent beacons, information regarding the ambulatory route itself may be programmed such that it is known by the system that a direct path 96, such as between beacon 92C and 92D or 92D and 92E, is not possible due to the physical constraints of the hallway of the short route 18 itself. In such an instance, an algorithm executed by the patient tracking computer may assign a probability of 0% to a direct path between beacons 92C and 92D, or any other possible path that intersects the wall of the hallway. Thus, the ambulation distance respectively between beacons 92C and 92D or 92D and 92E must compensate for the corner of the hallways that must be traversed by the patient. As with the example above, a favored or most probable path between 92C and 92D (and an associated distance) may be identified through the analysis of historical patient location information.

A still further example of intermittent beacon interpretation is represented by group 98 of beacons 92F, 92G, and 92H. Since each of the beacons in group 98 are within close proximity to one another, the location services system may interpret this group 98 in a variety of ways. In one embodiment, the location services system may interpret that the patient has moved great distances between consecutive beacons, however, was in roughly the same position each time that these beacons were obtained. Alternatively, the location services system may interpret that the patient has remained generally still and thus little total distance was traversed during this time interval. As with the interpretation regarding the bathroom 94, compiled ambulatory data from a plurality of historical patients traversing the short ambulatory route 18 may be used to provide statistical guidance with respect to the proper interpretation of beacon group 98.

It is unlikely that a slowly moving patient would quickly cover distances back and forth while beacons are obtained at roughly the same position. Therefore, an exemplary patient location algorithm may assign a low probability of 5% to that analysis. Alternatively, the analysis of historical patient location information may identify that such a group 98 or pattern of position beacons likely (80%) can be interpreted that the patient paused during the ambulatory event, for example to converse with another patient or a caregiver. In this exemplary embodiment the location services system may assume that beacon group 98 is a result of the patient stopping, and process the beacon group 98 by removing the two "unused" intervals (namely 92F-92G and 92G-92H) from the ambulatory event and simply interpret the event as though the patient moved from beacon 92E to beacon 92F and then to beacon 92I. Alternative embodiments of the location services system may include a most probable path that incorporates all of the beacons of beacon group 98. This would have the effect of increasing the calculated time required by the patient to complete the ambulatory event while minimally increasing the distance covered. These adjustments would result in a lowered calculated average speed over the course of the ambulatory event.

Figure 4:
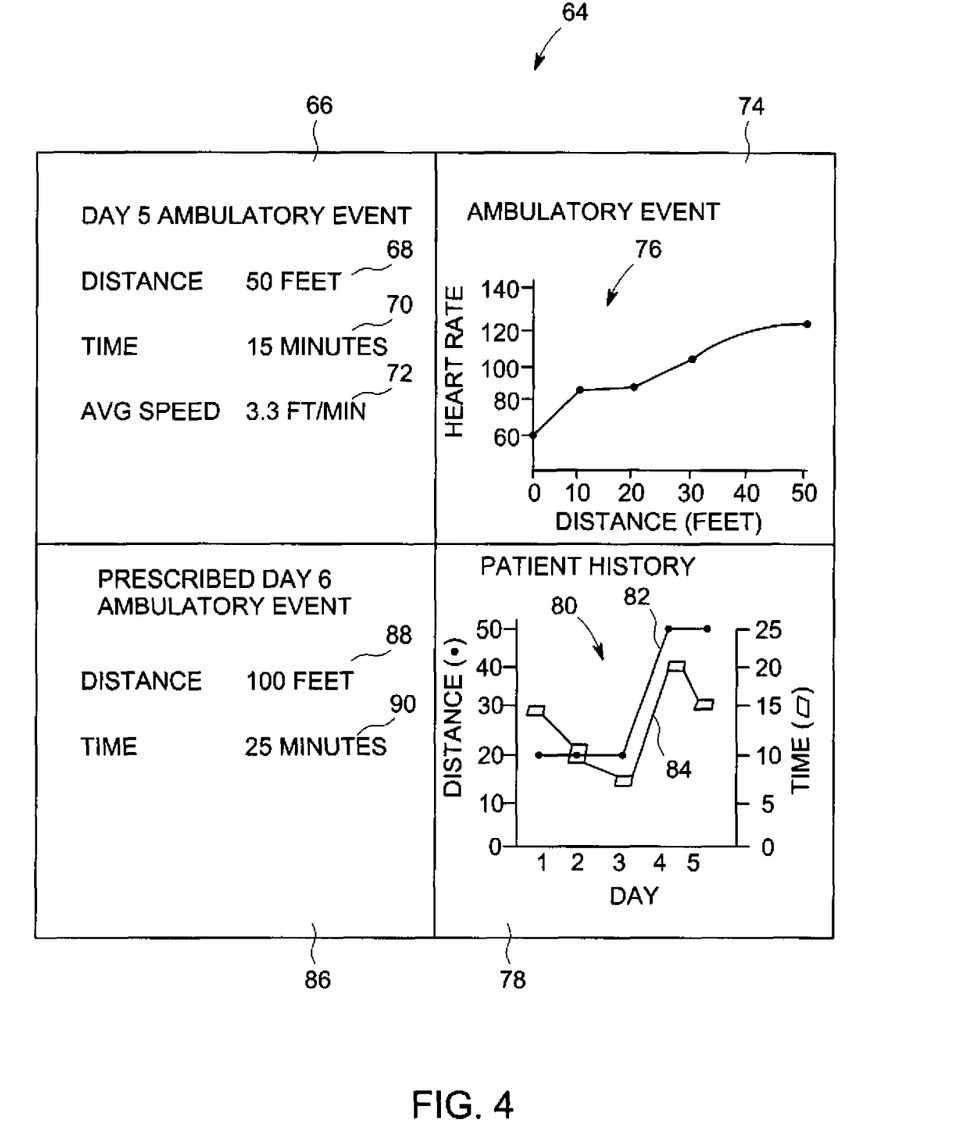
FIG. 4 depicts an exemplary embodiment of a graphical user interface used in connection with embodiments of the system and method.

FIG. 4 depicts an embodiment of a graphical user interface (GUI) 64 that may be presented on the graphical display 46 (FIGS. 2 and 3). The GUI 64 depicts exemplary embodiments of the ambulatory event data that may be presented on the graphical display 46. The merely exemplary GUI 64 is divided into four regions that each generally represent a different type of ambulatory event data that may be presented on the GUI 64. It is to be understood that alternative embodiments of the GUI 64 may include more or fewer of these types of ambulatory event data.

Region 66 identifies information regarding the current day's (exemplarily Day 5) ambulatory event. This includes reporting a distance 68 traveled by the patient during the ambulatory event. A time 70 is reported for the patient to complete the prescribed ambulatory event. Finally, an average speed 72 is calculated from the distance 68 and time 70 and reported in region 66.

Region 74 presents a graph 76 depicting a comparison between a physiological value and ambulatory event data from the Day 5 ambulatory event. The chart depicts the change in a patient's heart rate over the course of this single ambulatory event. The progress of the ambulatory event may be represented in terms of distance (feet) as in graph 76. Alternatively, the ambulatory event progress may be represented in terms of event duration (time). As represented in the graph 76, over the course of the ambulatory event the patient's heart rate increases from approximately 60 beats per minute to approximately 120 beats per minute. However, the graph 76 also shows that this increase is step-wise with plateaus rather than a steady increase. This graphical representation of the change in the patient's heart rate may provide assistance in evaluating patient condition as the patient's physiological response in the form of heart rate is correlated to the stress of the prescribed ambulatory event.

Region 78 presents a historical representation of a series of daily ambulatory events. This graphic may be obtained from information in the patient's EMR. Region 78 includes a chart 80 that reports the varying distances and times for each daily ambulatory event of the patient. Looking at the distance graph 82, it can be seen that the ambulatory event distance increased from 20 feet to 50 feet between Day 3 and Day 4. By reviewing the distance graph 82 with the context provided by the time graph 84, it can be readily identified that the patient's time to complete the prescribed 20 foot ambulatory event steadily decreases from 15 minutes to 7 minutes. After the patient completed the 20 foot ambulatory event on Day 3 in 7 minutes, the distance for the ambulatory event in Day 4 was increased to 50 feet. While the specific distances and times used in the present description are merely exemplary, this example shows how an improvement in patient performance in a prescribed ambulatory event over time can result in adjusting the ambulatory event in order to continue the patient's recovery process. This recovery process can also be noted in the decrease in time for the patient to complete the 50 foot ambulatory event between Day 4 and Day 5.

The graphical depiction of historical ambulatory event data as presented in chart 80 can be a useful tool for presenting patient condition and recovery to patients, or their family and friends who do not have medical training. By relating patient recovery and improvement to a real world task, such as an ambulatory event (walking a defined distance), patients and others presented with this data, may have a better understanding of their physiological condition. The graphical presentation of the ambulatory event data can provide a goal or other motivation in order to improve. Such improvement is visually seen and reinforced with each decrease in time for the completion of an ambulatory event. The patient is rewarded and challenged due to their improvements by increasing the distance of the next ambulatory event.

Region 86 presents a prescribed ambulatory event for the next day (Day 6). Since the patient reduced the time needed to complete the 50 foot ambulatory event between Day 4 and Day 5, the prescribed ambulatory event for Day 6, presented in region 86, is established at a distance 88 of 100 feet. The prescribed completion time 90 for this ambulatory event is set at 25 minutes. This presents the patient with a new ambulatory goal, thus motivating the patient to continue progress towards recovery.

The GUI 64, presented in FIG. 4, thus provides a patient without medical training a visual report that shows current ambulatory performance in relation to physiological parameters and previous ambulatory event performance. This presentation of monitored physiological parameters in context with a real-world activity can facilitate an understanding of current medical status by the patient and motivate the patient to improve in ambulatory performance, aiding in recovery. The patient is further positively challenged by a prescribed ambulatory event that is based upon the patient's previous ambulatory event performance.

Relating FIG. 1 to FIG. 4, the short route 18 and the long route 20 depicted on the floor plan 10 of the telemetry ward, may relate to actual predetermined ambulatory event routes. In an exemplary embodiment, the short route 18 may represent a prescribed ambulatory event of a distance of 20 feet. Thus, when the patient is prescribed a 20 foot ambulatory event, the patient is instructed to follow the route A-B-F-G. In some telemetry wards, this may be represented by a physical line drawn with a specified color on the floor of the halls of the telemetry ward. Continuing with this example, the long route 20 may be representative of an ambulatory event distance of 50 feet. Therefore, when prescribed with a 50 foot ambulatory event, the patient will follow the route A-B-C-D-E-F-G. For longer ambulatory events, the patient may combine routes or make multiple laps of defined routes. Therefore, for the prescribed Day 6 ambulatory event distance of 100 feet, the patient may be instructed to follow the long route 20 for two laps before completion. In another example, a 70 foot ambulatory event may be prescribed by completing one lap of the short route 18 and one lap of the long route 20; however, these are intended to be merely exemplary of prescribed ambulatory event routes.

Figure 5:
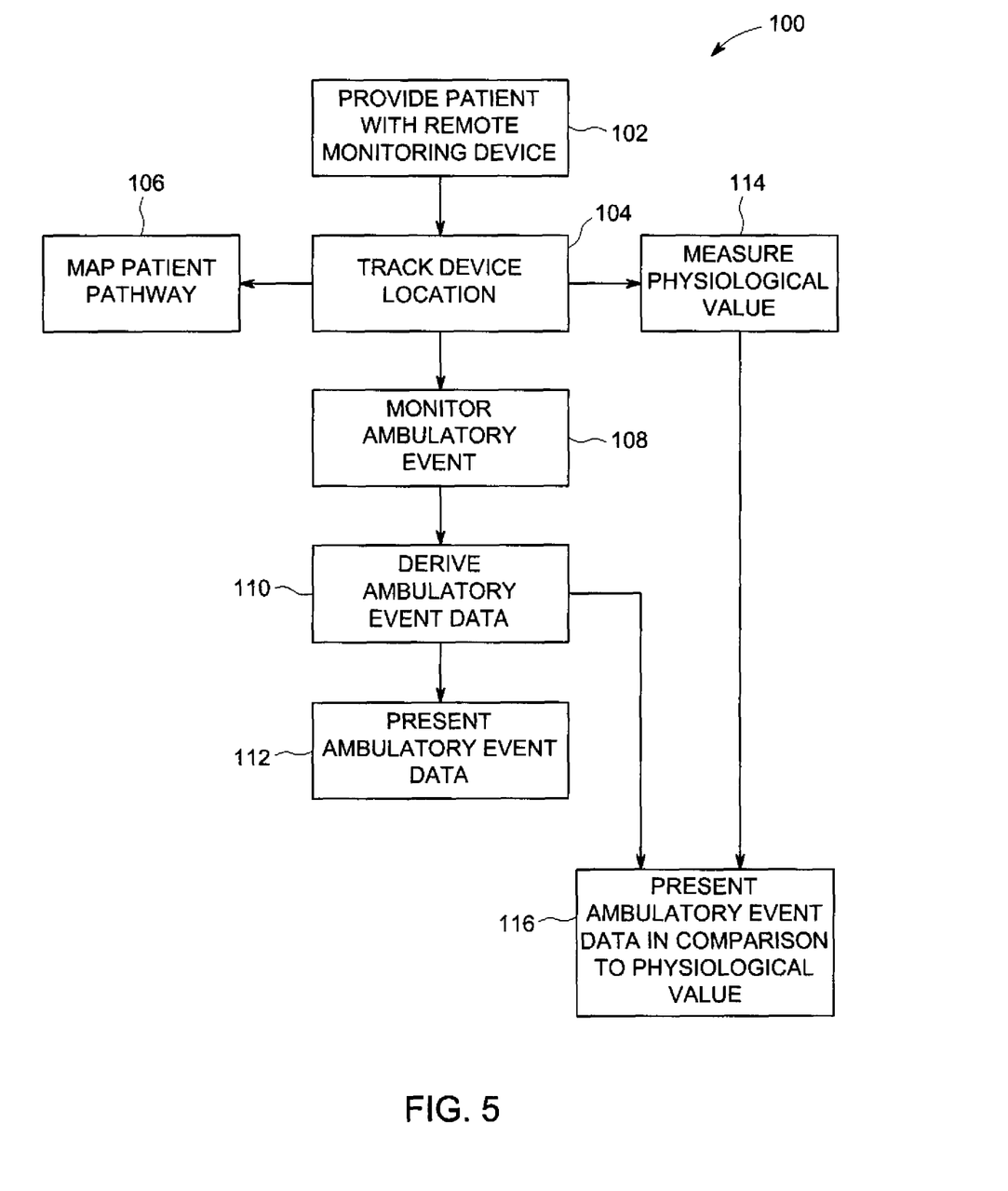
FIG. 5 is a flow chart depicting an embodiment of the method of monitoring an ambulatory patient.

FIG. 5 is a flow chart depicting an embodiment of a method of monitoring an ambulatory patient 100. The method 100 begins with providing the ambulatory patient with a remote monitoring device 102. As noted above, the remote monitoring device may be a wireless device that is attached to, located on, or associated with the patient. The remote monitoring device may be specifically designed to track patient location; however, alternative embodiments of the remote monitoring device may also monitor physiological parameters from the patient. Such physiological parameters may include, but are not limited to, heart rate, NIBP, ECG, and $SpO_2$.

At 104, the location of the remote monitoring device is tracked. As noted above, the tracking of the remote monitoring device location may be performed in a variety of manners by a location services system. The location services system may be based upon GPS coordinates that are transmitted from the remote monitoring device. Alternatively, the local services system may track a radio frequency (RF) or infrared (IR) signal from the remote monitoring device that is indicative of the location of the remote monitoring device. In some embodiments, the RF or IR signal may be triangulated by the location services system to track the device location. Additionally, the location services system may be a real-time location services (RTLS) system.

In an optional embodiment, a patient pathway may be tracked at 106 by the LS system. By concatenating a series of tracked device locations from 104 over time, a pathway of the patient during an ambulatory event may be mapped. The mapping of the patient pathway at 106 may be performed using a probability analysis as disclosed above using historical patient location information to provide a likelihood, which may be a percentage, that the patient took a particular path between detected location beacons. The mapped pathway may be stored for later reference, such as in the development of more detailed algorithms to interpret patient movement between location beacons. Alternatively, the mapped pathway may be presented on a graphical display to the patient or a clinician.

At 108, the ambulatory event is monitored with a patient tracking computer. The patient tracking computer receives the tracked location of the remote monitoring device from the LS system and monitors the device location over the course of the ambulatory event. The patient tracking computer may apply one or more algorithms derived from historical patient location information to calculate a distance traveled between location beacons over the course of the ambulatory event. In some embodiments, monitoring the ambulatory event includes determining a start of an ambulatory event and an end of an ambulatory event and monitoring the device location during the ambulatory event.

Next, at 110, the patient tracking computer derives ambulatory event data from the tracked locations across the ambulatory event. As noted above, the ambulatory event data may include a variety of data, including: a distance traveled during the ambulatory event, a duration of the ambulatory event, and an average speed across the ambulatory event; however, these are not intended to be limiting on the types of ambulatory event data that may be derived by the patient tracking computer at 110.

At 112, the ambulatory event data derived at 110 is presented to a patient or clinician. The presentation of the ambulatory event data at 112 may be performed by a graphical display and may be presented in the form of a GUI or may alternatively be presented to the patient or clinician in a textual format as sent in e-mail or SMS communications.

In an alternative embodiment, while the remote monitoring device location is tracked at 104, the remote monitoring device is also measuring a physiological value from the patient at 114. The remote monitoring device transmits the measured physiological value to the patient tracking computer. In one embodiment, the LS system uses the transmission signal of the transmitted physiological value from the remote monitoring device in order to triangulate and track the remote monitoring device location at 104.

After the physiological value has been measured and transmitted to the patient tracking computer, the patient tracking computer at 116 presents the ambulatory event data and the physiological value in a comparative format. As noted above with respect to 112, the presentation of the ambulatory event data and the physiological value in a comparative format may be performed by a graphical display using a GUI or textual based communication.

As noted above, the comparative presentation of ambulatory event data and physiological values may relate a change in physiological value over the progress or course of the ambulatory event. In one non-limiting example, at 116, the patient is presented with a plurality of $SpO_2$ values measured during the course of an ambulatory event. The $SpO_2$ values are presented in relation to the progress of the patient in the ambulatory event such as determined by distance traveled or ambulatory event duration.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of monitoring an ambulatory patient, the method comprising:
   providing the ambulatory patient with a remote monitoring device;
   presenting the patient with a prescribed ambulation distance;
   tracking a plurality of locations of the remote monitoring device with a location services (LS) system;
   monitoring an ambulatory event with a patient tracking computer communicatively connected to the remote monitoring device and the LS system;
   identifying a plurality of possible paths between a first location of the plurality of locations of the remote monitoring device and a second location of the plurality of locations of the remote monitoring device;
   selecting a path from the plurality of possible paths between the first location of the plurality of locations and the second location of the plurality of locations;
   deriving ambulatory event data from the tracked plurality of locations and the selected path, the ambulatory event data comprising an ambulatory event distance and an ambulatory event duration;
   comparing the plurality of locations of the remote monitoring device tracked by the LS system to the prescribed ambulation distance; and
   presenting, to the ambulatory patient on a graphical display, the ambulatory event data and the prescribed ambulation distance.

2. The method of claim 1, further comprising mapping a patient pathway during the ambulatory event.

3. The method of claim 1, further comprising measuring a plurality of physiological values of at least one physiological value type from the patient with the remote monitoring device.

4. The method of claim 3, further comprising:
broadcasting the plurality of physiological values from the remote monitoring device; and
triangulating the broadcast physiological values with the LS system, wherein the LS system tracks the plurality of locations from the triangulated broadcast physiological value.

5. The method of claim 3, wherein the at least one physiological value type comprises at least one of heart rate, blood pressure, electrocardiogram, and SpO2.

6. The method of claim 3, further comprising presenting, on a graphical display, the ambulatory event data in comparison to the physiological value.

7. The method of claim 1, further comprising:
recording ambulatory event data for a plurality of previous ambulatory events;
presenting current ambulatory event data derived from a current ambulatory event on the graphical display in comparison to ambulatory event data for at least one previous ambulatory event.

8. The method of claim 7, further comprising presenting a trend in ambulatory event data from a plurality of previous ambulatory events and the current ambulatory event data on the graphical display.

9. The method of claim 7, further comprising:
presenting, on the graphical display, ambulatory event data from a plurality of previous ambulatory events of the same prescribed ambulation.

10. The method of claim 1, further comprising determining an ambulatory event start and an ambulatory event end from the tracked plurality of locations, wherein the ambulatory event data is derived from the ambulatory event start and the ambulatory event end.

11. The method of claim 1, further comprising recording the ambulatory event data in an electronic medical record (EMR) of the patient.

12. The method of claim 1, wherein ambulatory event data further comprises at least one of average speed and instantaneous speed.

13. A method of monitoring a patient, the method comprising:
providing the ambulatory patient with a remote monitoring device;
measuring a plurality of physiological values of at least one type of physiological value with the remote monitoring device;
tracking a plurality of locations of the remote monitoring device over time with the location services (LS) system;
monitoring an ambulatory event with a patient tracking computer communicatively connected to the remote monitoring device and the LS system;
receiving the plurality of physiological values from the remote monitoring device;
determining an ambulatory event start and an ambulatory event end from the tracked plurality of locations;
identifying a plurality of possible paths between a first location of the plurality of locations of the remote monitoring device and a second location of the plurality of locations of the remote monitoring device;
selecting a path from the plurality of possible paths between the first location of the plurality of locations and the second location of the plurality of locations;
deriving ambulatory event data from the tracked plurality of locations, the selected path, the ambulatory event start, and the ambulatory event end, the ambulatory event data comprising an ambulatory event distance and an ambulatory event duration; and
presenting the ambulatory event data and at least one physiological value of the plurality of physiological values to the patient on a graphical display.

14. The method of claim 13, further comprising:
broadcasting the plurality of physiological values from the remote monitoring device;
receiving the broadcasted plurality of physiological values at a plurality of telemetry receivers of a location services (LS) system;
triangulating the broadcasted physiological values with the LS system to determine the plurality of locations of the remote monitoring device;
measuring signal strengths of the received broadcasted plurality of physiological values received at each of the plurality of telemetry receivers; and
determining the plurality of locations of the remote monitoring device based upon the measured signal strengths.

15. The method of claim 13, further comprising:
presenting the patient with a prescribed ambulation;
comparing the plurality of locations of the remote monitoring device tracked by the LS system to the prescribed ambulation; and
presenting the prescribed ambulation on the graphical display.

16. The method of claim 13, wherein deriving ambulatory event data comprises calculating a distance traveled by the patient from the tracked plurality of locations between the ambulatory event start and the ambulatory event end.

17. The method of claim 16, further comprising:
calculating a probability that the remote monitoring device traveled a possible path associated with each of the plurality of possible paths wherein the selected path is a most probable path from the plurality of possible paths; and
calculating the distance traveled by the patient based upon a distance of the selected path.

18. The method of claim 13, further comprising recording the ambulatory event data in an electronic medical record (EMR) of the patient.

19. The method of claim 13, wherein ambulatory event data further comprises at least one of average speed and instantaneous speed.

20. The method of claim 1, wherein the remote monitoring device further comprises a global positioning system (GPS) and comprising:
determining the plurality of locations of the remote monitoring device with the GPS; and
providing the plurality of locations from the remote monitoring device to the LS system.

* * * * *